United States Patent
Ichinose

(10) Patent No.: US 11,978,274 B2
(45) Date of Patent: May 7, 2024

(54) DOCUMENT CREATION SUPPORT APPARATUS, DOCUMENT CREATION SUPPORT METHOD, AND DOCUMENT CREATION SUPPORT PROGRAM

(71) Applicant: FUJIFILM Corporation, Tokyo (JP)

(72) Inventor: Akimichi Ichinose, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/748,017

(22) Filed: May 18, 2022

(65) Prior Publication Data

US 2022/0277577 A1 Sep. 1, 2022

Related U.S. Application Data

(63) Continuation of application No. PCT/JP2020/044238, filed on Nov. 27, 2020.

(30) Foreign Application Priority Data

Nov. 29, 2019 (JP) ................. 2019-217419

(51) Int. Cl.
*G06V 30/416* (2022.01)
*G06V 30/12* (2022.01)
(Continued)

(52) U.S. Cl.
CPC ............ *G06V 30/416* (2022.01); *G06V 30/12* (2022.01); *G06V 30/18143* (2022.01); *G06V 30/19007* (2022.01)

(58) Field of Classification Search
CPC ................. G06V 30/416; G06V 30/12; G06V 30/18143; G06V 30/19007; G06V 2201/03; G16H 15/00
See application file for complete search history.

(56) References Cited

U.S. PATENT DOCUMENTS 7,804,990 B2 * 9/2010 Kiraly ....................... G06T 7/73
382/128
9,922,268 B2 3/2018 Iwamura et al.
(Continued)

FOREIGN PATENT DOCUMENTS

JP 2013039230 2/2013
JP 2015187845 10/2015
(Continued)

OTHER PUBLICATIONS

Geoffrey D. Rubin et al., "Pulmonary Nodules on Multi-Detector Row CT Scans: Performance Comparison of Radiologists and Computer-aided Detection," Radiology, vol. 234, Jan. 2005, pp. 274-283.
(Continued)

*Primary Examiner* — Aaron W Carter
(74) *Attorney, Agent, or Firm* — JCIPRNET

(57) ABSTRACT

A document creation support apparatus comprising at least one processor, wherein the processor is configured to: acquire an image and a character string related to the image; extract at least one feature region included in the image; specify a specific region that is a region corresponding to a phrase included in the character string, in the feature region; and present information for supporting creation of a document including the character string based on a result of the specifying.

9 Claims, 13 Drawing Sheets

(51) Int. Cl.
    *G06V 30/18*    (2022.01)
    *G06V 30/19*    (2022.01)

(56) References Cited

U.S. PATENT DOCUMENTS

| | | | | |
|---|---|---|---|---|
| 11,238,974 | B2* | 2/2022 | Yokokubo | G16H 30/20 |
| 11,244,755 | B1* | 2/2022 | Syeda-Mahmood | G06N 3/04 |
| 2005/0107690 | A1* | 5/2005 | Soejima | G16H 30/20 600/425 |
| 2006/0239394 | A1* | 10/2006 | Fujieda | G06F 16/5866 378/1 |
| 2006/0277073 | A1* | 12/2006 | Heilbrunn | G16H 15/00 705/3 |
| 2009/0087049 | A1* | 4/2009 | Takahashi | G16H 15/00 382/128 |
| 2009/0310836 | A1* | 12/2009 | Krishnan | G06T 7/0012 382/128 |
| 2011/0002515 | A1* | 1/2011 | Futami | G16H 15/00 382/128 |
| 2011/0075913 | A1* | 3/2011 | Moriya | G16H 30/40 382/132 |
| 2013/0268555 | A1* | 10/2013 | Utsunomiya | G16H 10/60 707/769 |
| 2015/0324521 | A1* | 11/2015 | Yokokubo | G16H 30/00 705/3 |
| 2017/0017718 | A1 | 1/2017 | Nakayama et al. | |
| 2017/0069084 | A1* | 3/2017 | Kubo | G06V 10/26 |
| 2017/0300664 | A1* | 10/2017 | Matsuki | G16H 30/20 |
| 2019/0139218 | A1* | 5/2019 | Song | G06N 3/044 |
| 2019/0188848 | A1* | 6/2019 | Madani | G16H 30/40 |
| 2019/0237184 | A1* | 8/2019 | Sharma | G06F 40/289 |
| 2019/0267120 | A1* | 8/2019 | Hirakawa | G16H 15/00 |
| 2019/0279408 | A1* | 9/2019 | Hirakawa | G06T 11/60 |
| 2019/0279751 | A1 | 9/2019 | Nakamura et al. | |
| 2019/0295248 | A1 | 9/2019 | Nakamura et al. | |
| 2019/0325249 | A1 | 10/2019 | Tahmasebi et al. | |
| 2019/0333218 | A1* | 10/2019 | Bronkalla | G06T 7/0014 |
| 2020/0043600 | A1* | 2/2020 | Glottmann | G16H 15/00 |
| 2020/0219609 | A1* | 7/2020 | Harte | G16H 15/00 |
| 2021/0012870 | A1* | 1/2021 | Hirakawa | G06F 40/166 |
| 2021/0027872 | A1* | 1/2021 | Hirakawa | A61B 5/00 |
| 2021/0074427 | A1* | 3/2021 | Xu | G16H 50/20 |
| 2021/0166807 | A1* | 6/2021 | Quennesson | G06T 7/0012 |
| 2021/0216822 | A1* | 7/2021 | Paik | G16H 15/00 |
| 2021/0287054 | A1* | 9/2021 | Zhang | G06F 18/241 |
| 2022/0013205 | A1* | 1/2022 | Hasegawa | G16H 10/60 |
| 2022/0262471 | A1* | 8/2022 | Nakamura | G16H 50/20 |
| 2022/0277577 | A1* | 9/2022 | Ichinose | G06V 30/12 |
| 2022/0285011 | A1* | 9/2022 | Nakamura | G06V 10/764 |
| 2022/0366151 | A1* | 11/2022 | Nakamura | G06F 3/0482 |
| 2022/0375562 | A1* | 11/2022 | Nakamura | G06T 7/0012 |
| 2022/0392595 | A1* | 12/2022 | Ichinose | G16H 50/30 |
| 2022/0392619 | A1* | 12/2022 | Ichinose | G16H 30/40 |
| 2022/0415459 | A1* | 12/2022 | Ichinose | G16H 50/30 |
| 2023/0005252 | A1* | 1/2023 | Qadir | G06V 10/7747 |
| 2023/0005580 | A1* | 1/2023 | Momoki | G06T 7/0012 |
| 2023/0005601 | A1* | 1/2023 | Nakamura | G16H 50/70 |

FOREIGN PATENT DOCUMENTS

| | | |
|---|---|---|
| JP | 2017021648 | 1/2017 |
| JP | 2019149005 | 9/2019 |
| JP | 2019153250 | 9/2019 |
| JP | 2019169049 | 10/2019 |

OTHER PUBLICATIONS

Kuang-Huei Lee et al., "Stacked Cross Attention for Image-Text Matching," European Conference on Computer Vision (ECCV), Oct. 2018, pp. 1-16.

"International Search Report (Form PCT/ISA/210) of PCT/JP2020/044238," dated Feb. 16, 2021, with English translation thereof, pp. 1-5.

"Written Opinion of the International Searching Authority (Form PCT/ISA/237)" of PCT/JP2020/044238, dated Feb. 16, 2021, with English translation thereof, pp. 1-7.

"Office Action of Japan Counterpart Application", dated Jul. 11, 2023, with English translation thereof, p. 1-p. 16.

"Office Action of Japan Counterpart Application", dated Oct. 17, 2023, with English translation thereof, p. 1-p. 10.

"Decision of Refusal of Japan Counterpart Application No. 2021-561545", issued on Mar. 19, 2024, with English translation thereof, p. 1-p. 2.

"Decision of Dismissal of Amendment of Japan Counterpart Application No. 2021-561545", issued on Mar. 19, 2024, with English translation thereof, p. 1-p. 7.

* cited by examiner

DOCUMENT CREATION SUPPORT APPARATUS, DOCUMENT CREATION SUPPORT METHOD, AND DOCUMENT CREATION SUPPORT PROGRAM

CROSS REFERENCE TO RELATED APPLICATIONS

The present application is a Continuation of PCT International Application No. PCT/JP2020/044238, filed on Nov. 27, 2020, which claims priority to Japanese Patent Application No. 2019-217419, filed on Nov. 29, 2019. Each application above is hereby expressly incorporated by reference, in its entirety, into the present application.

BACKGROUND

Technical Field

The present disclosure relates to a document creation support apparatus, a document creation support method, and a document creation support program that support the creation of documents such as interpretation reports.

Related Art

In recent years, advances in medical devices, such as computed tomography (CT) apparatuses and magnetic resonance imaging (MRI) apparatuses, have enabled image diagnosis using high-resolution medical images with higher quality. In particular, since a region of a lesion can be accurately specified by image diagnosis using CT images, MRI images, and the like, appropriate treatment is being performed based on the specified result.

In addition, there is another image diagnosis where medical images are analyzed by computer-aided diagnosis (CAD) using a discriminator trained by deep learning or the like, regions, positions, volumes, and the like of lesions or the like included in the medical images are extracted, and the extracted ones are acquired as an analysis result (for example, "Pulmonary Nodules on Multi-Detector Row CT Scans: Performance Comparison of Radiologists and Computer-aided Detection", Rubin G D et al., In Radiology 2005; 234: 274 to 283 (hereinafter referred to as "Literature 1")). In this way, the analysis result generated by the analysis process is saved in a database in association with examination information, such as a patient name, gender, age, and an imaging apparatus which has acquired a medical image, and is provided for diagnosis. In this case, a radiology technician or the like who has acquired a medical image determines a radiologist according to the medical image and informs the determined radiologist that the medical image and CAD analysis results are present. The radiologist interprets the medical image by referring to the distributed medical image and analysis result and creates an interpretation report, in his or her own interpretation terminal.

Further, a technique for presenting sentence candidates by extracting sentences including input characters from a report database based on the input characters at the time of creating an interpretation report is disclosed (for example, see JP2017-021648A).

A radiologist may interpret a plurality of tomographic images obtained by one imaging with an imaging apparatus such as a CT apparatus and an MRI apparatus, and describe the findings obtained from the respective tomographic images in an interpretation report. In this case, it is desired to create the interpretation report so that it can be seen from which tomographic image the findings described in the image interpretation report can be recognized. However, creating the interpretation report manually by the radiologist is a burden on the interpretation work.

Further, the number of medical images to be interpreted is increasing with the improvement of the performance of the imaging apparatuses such as the CT apparatus and the MRI apparatus described above, and thus it is desired to support the suppression of oversight of findings and misdiagnosis.

SUMMARY

The present disclosure is to provide a document creation support apparatus, a document creation support method, and a document creation support program capable of supporting the creation of documents such as interpretation reports.

According to a first aspect of the present disclosure, there is provided a document creation support apparatus comprising at least one processor, and the processor is configured to acquire an image and a character string related to the image, extract at least one feature region included in the image, specify a specific region that is a region corresponding to a phrase included in the character string, in the feature region, and present information for supporting creation of a document including the character string based on a result of the specifying.

According to a second aspect of the present disclosure, in the above aspect, the processor may be configured to embed information for accessing an image including the specific region in a phrase corresponding to the specific region in the character string, and display the information on a display unit.

According to a third aspect of the present disclosure, in the document creation support apparatus of the above aspect, the processor may be configured to generate property information indicating a property of the specific region, and display the property information on a display unit.

According to a fourth aspect of the present disclosure, in the document creation support apparatus of the above aspect, the processor may be configured to generate property information indicating a property of the specific region, and give a warning in a case where a phrase related to the specific region in the character string does not match the property information.

According to a fifth aspect of the present disclosure, in the document creation support apparatus of the above aspect, the processor may be configured to generate an image in which a mark indicating a position of the specific region is added to an image including the specific region.

According to a sixth aspect of the present disclosure, in the document creation support apparatus of the above aspect, the processor may be configured to extract the feature region based on at least one of a position, type, or size of a structure included in the image.

According to a seventh aspect of the present disclosure, there is provided a document creation support method comprising: acquiring an image and a character string related to the image; extracting at least one feature region included in the image; specifying a specific region that is a region corresponding to a phrase included in the character string, in the feature region; and presenting information for supporting creation of a document including the character string based on a result of the specifying.

According to an eighth aspect of the present disclosure, there is provided a document creation support program for causing a computer to execute a process comprising: acquiring an image and a character string related to the image;

extracting at least one feature region included in the image; specifying a specific region that is a region corresponding to a phrase included in the character string, in the feature region; and presenting information for supporting creation of a document including the character string based on a result of the specifying.

According to the above aspects, a document creation support apparatus, a document creation support method, and a document creation support program of the present disclosure can support creation of documents such as interpretation reports.

DETAILED DESCRIPTION

Hereinafter, each exemplary embodiment of the present disclosure will be described with reference to the drawings.

First Exemplary Embodiment

First, a configuration of the medical information system 1 to which a document creation support apparatus of the present disclosure is applied will be described.

Figure 1:
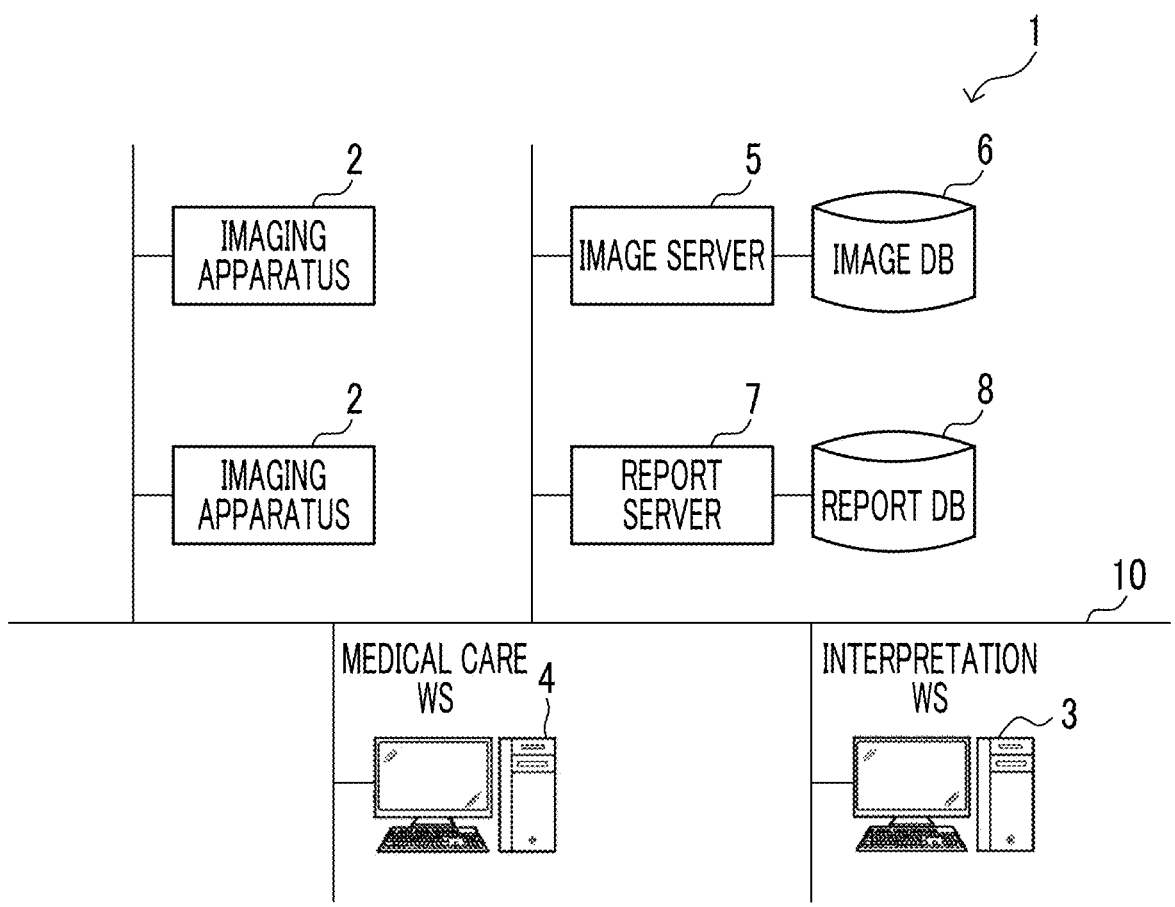
FIG. 1 is a diagram showing an example of a schematic configuration of a medical information system according to each exemplary embodiment.

FIG. 1 is a diagram showing a schematic configuration of the medical information system 1. The medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

As shown in FIG. 1, the medical information system 1 is configured to include a plurality of imaging apparatuses 2, a plurality of interpretation work stations (WS) 3 that are interpretation terminals, a medical care WS 4, an image server 5, an image database (DB) 6, a report server 7, and a report DB 8, which are connected via a wired or wireless network 10 so as to be able to communicate with each other.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 10 or in a network storage in a state in which it can be accessed from the outside, and is downloaded and installed on the computer in response to a request.

The imaging apparatus 2 is an apparatus (modality) that generates a medical image showing a diagnosis target part of the subject by imaging the diagnosis target part. Specifically, examples of the imaging apparatus include a simple X-ray imaging apparatus, a CT apparatus, an MRI apparatus, a positron emission tomography (PET) apparatus, and the like. The medical image generated by the imaging apparatus 2 is transmitted to the image server 5 and is saved in the image DB 6.

The interpretation WS 3 is a computer used by, for example, a radiologist of the radiology department to interpret a medical image and to create an image interpretation report, and encompasses a document creation support apparatus 20 (which will be described in detail later) according to the present exemplary embodiment. In the interpretation WS 3, a viewing request for a medical image to the image server 5, various image processing for the medical image received from the image server 5, display of the medical image, and input reception of comments on findings regarding the medical image are performed. In the interpretation WS 3, an analysis process for medical images and input comments on findings, support for creating an interpretation report based on the analysis result, a registration request and a viewing request for the interpretation report to the report server 7, and display of the interpretation report received from the report server 7 are performed. The above processes are performed by the interpretation WS 3 executing software programs for respective processes.

The medical care WS 4 is a computer used by a doctor in a medical department to observe an image in detail, view an interpretation report, create an electronic medical record, and the like, and is configured to include a processing apparatus, a display apparatus such as a display, and an input apparatus such as a keyboard and a mouse. In the medical care WS 4, a viewing request for the image to the image server 5, display of the image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 comprises a storage in which the image DB 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the imaging apparatus 2, the image server 5 prepares the medical image in a format for a database and registers the medical image in the image DB 6.

Image data of the medical image acquired by the imaging apparatus 2 and accessory information are registered in the image DB 6. The accessory information includes, for example, an image identification (ID) for identifying each medical image, a patient ID for identifying a subject, an examination ID for identifying an examination, a unique ID (UID: unique identification) allocated for each medical image, examination date and examination time at which a medical image is generated, the type of imaging apparatus used in an examination for acquiring a medical image, patient information such as the name, age, and gender of a patient, an examination part (that is, imaging part), imaging information (for example, an imaging protocol, an imaging sequence, an imaging method, imaging conditions, the use of a contrast medium, and the like), and information such as a series number or a collection number in a case where a plurality of medical images are acquired in one examination.

In addition, in a case where the viewing request from the interpretation WS 3 and the medical care WS 4 is received through the network 10, the image server 5 searches for a medical image registered in the image DB 6 and transmits the searched for medical image to the interpretation WS 3 and the medical care WS 4 that are request sources.

The report server 7 incorporates a software program for providing a function of a database management system to a general-purpose computer. In a case where the report server 7 receives a request to register the interpretation report from the interpretation WS 3, the report server 7 prepares the interpretation report in a format for a database and registers the interpretation report in the report DB 8.

In the report DB 8, an interpretation report including at least the comments on findings created by the radiologist using the interpretation WS 3 is registered. The interpretation report may include, for example, information such as a medical image to be interpreted, an image ID for identifying the medical image, a radiologist ID for identifying the radiologist who performed the interpretation, a lesion name, a lesion position information, information for accessing a medical image including a specific region (which will be described in detail later), and property information (which will be described in detail later).

Further, in a case where the report server 7 receives the viewing request for the interpretation report from the interpretation WS 3 and the medical care WS 4 through the network 10, the report server 7 searches for the interpretation report registered in the report DB 8, and transmits the searched for interpretation report to the interpretation WS 3 and the medical care WS 4 that are request sources.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Next, the document creation support apparatus 20 according to the present exemplary embodiment will be described.

Figure 2:
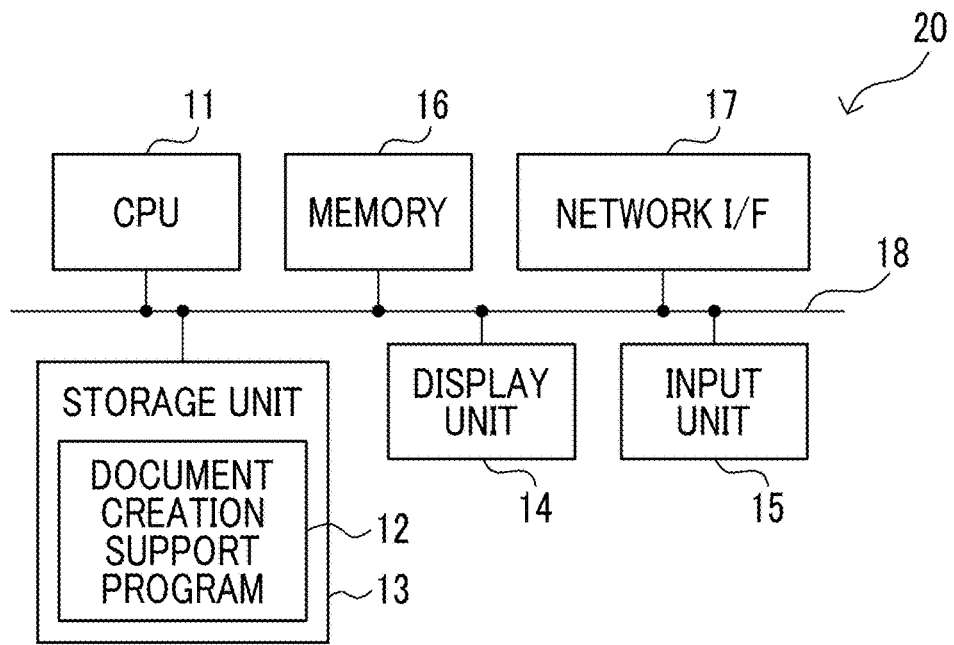
FIG. 2 is a block diagram showing an example of a hardware configuration of a document creation support apparatus according to each exemplary embodiment.

First, with reference to FIG. 2, a hardware configuration of the document creation support apparatus 20 according to the present exemplary embodiment will be described. As shown in FIG. 2, the document creation support apparatus 20 includes a central processing unit (CPU) 11, a non-volatile storage unit 13, and a memory 16 as a temporary storage area. Further, the document creation support apparatus 20 includes a display unit 14 such as a liquid crystal display, an input unit 15 such as a keyboard and a mouse, and a network interface (I/F) 17 connected to the network 10. The CPU 11, the storage unit 13, the display unit 14, the input unit 15, the memory 16, and the network I/F 17 are connected to a bus 18. The CPU 11 is an example of a processor in the present disclosure.

The storage unit 13 is realized by a hard disk drive (HDD), a solid state drive (SSD), a flash memory, and the like. A document creation support program 12 is stored in the storage unit 13 as a storage medium. The CPU 11 reads the document creation support program 12 from the storage unit 13, loads the read document creation support program 12 into the memory 16, and executes the loaded document creation support program 12.

Figure 3:
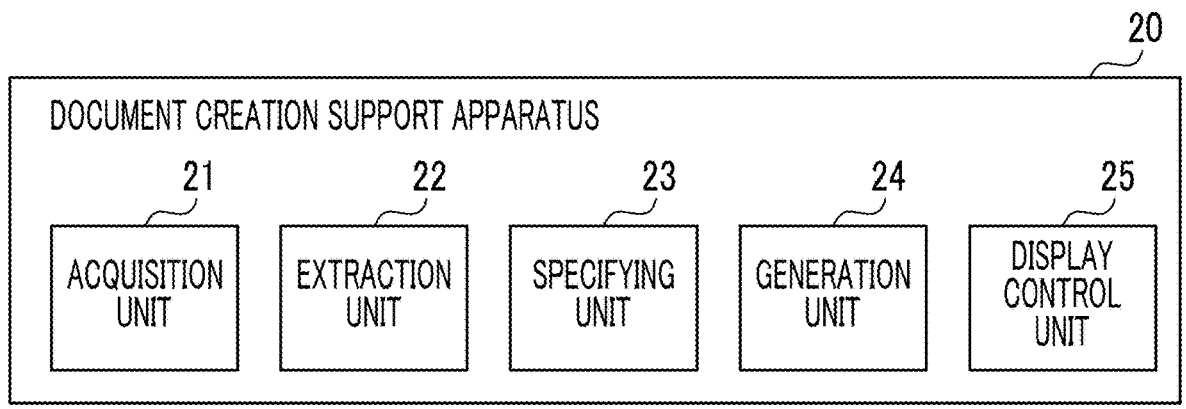
FIG. 3 is a block diagram showing an example of a functional configuration of the document creation support apparatus according to each exemplary embodiment.

Next, with reference to FIGS. 3 to 6, a functional configuration of the document creation support apparatus 20 according to the present exemplary embodiment will be described. As shown in FIG. 3, the document creation support apparatus 20 includes an acquisition unit 21, an extraction unit 22, a specifying unit 23, a generation unit 24, and a display control unit 25. The CPU 11 executing the document creation support program 12 functions as the acquisition unit 21, the extraction unit 22, the specifying unit 23, the generation unit 24, and the display control unit 25.

The acquisition unit 21 acquires a medical image G0 as an example of the image from the image server 5 via the network I/F 17. Further, the acquisition unit 21 acquires comments on findings as an example of a character string relating to the medical image G0 input by the radiologist via the input unit 15.

Figure 4:
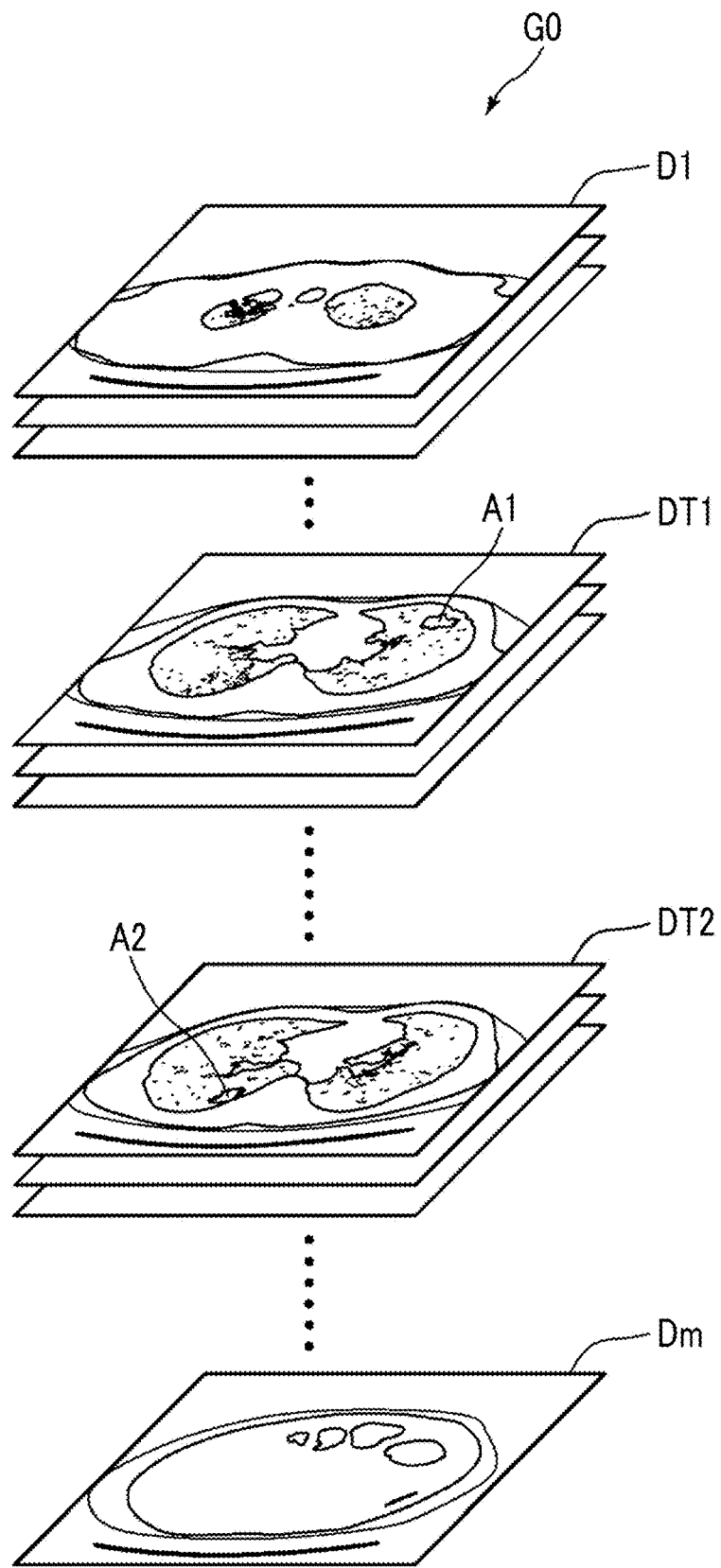
FIG. 4 is a diagram schematically showing a medical image.

FIG. 4 is a diagram schematically showing the medical image G0. In the present exemplary embodiment, as an example, a CT image of a lung consisting of m tomographic images D1 to Dm (m is 1 or more) is used as the medical image G0. In the medical image G0, a tomographic image DT1 contains a nodular shadow A1, and a tomographic image DT2 contains an infiltration shadow A2.

The extraction unit 22 extracts at least one feature region included in the medical image G0. In this case, the extraction unit 22 extracts the feature region based on at least one of a position, type, or size of a structure included in the medical image G0. The feature region refers to a region of an imaged feature, including, for example, an abnormal shadow such as the nodular shadow A1 and the infiltration shadow A2 as an example of a structure. For example, the extraction unit 22 analyzes the medical image G0 via CAD or the like, extracts the feature region containing the nodular shadow A1 from the tomographic image DT1, and extracts the feature region including the infiltration shadow A2 from the tomographic image DT2. As a method for extracting the feature region via the extraction unit 22, for example, a method described in Literature 1 above can be used, but the method is not limited thereto.

In the present exemplary embodiment, the information on the feature region extracted by the extraction unit 22 includes information on the size and position of the abnormal shadow. The size of the abnormal shadow can be expressed by the vertical and horizontal sizes of each abnormal shadow. Further, the diameter at the time when the abnormal shadow is approximated to a circle may be used as the size. The position of the abnormal shadow can be, for example, the centroid position of the abnormal shadow in each tomographic image. Further, as information on the size and position of the abnormal shadow, coordinates of the four corners of a rectangle including the abnormal shadow may be used.

The specifying unit 23 specifies a specific region, which is a region corresponding to a phrase included in the comments on findings, in the feature region extracted by the extraction unit 22. As a method for specifying the specific region via the specifying unit 23, for example, the method described in "Stacked Cross Attention for Image-Text Matching", (Kuang-Huei Lee et al., In European Conference on Computer Vision (ECCV), 2018) can be used. The above Literature discloses a technique for specifying a region in an image that is meant by each word in a sentence by analyzing the similarity of each combination of a plurality of regions in the image with respective different features and a plurality of words in the sentence. The method for specifying the specific region via the specifying unit 23 is not limited to that mentioned above.

The generation unit 24 generates information (hereinafter, referred to as "support information") for supporting the creation of an interpretation report based on the result specified by the specifying unit 23. The display control unit 25 displays an interpretation report creation screen 30 on the display unit 14, and controls the display content of the creation screen 30 based on the support information generated by the generation unit 24. The support information will be described in detail later.

Figure 5:
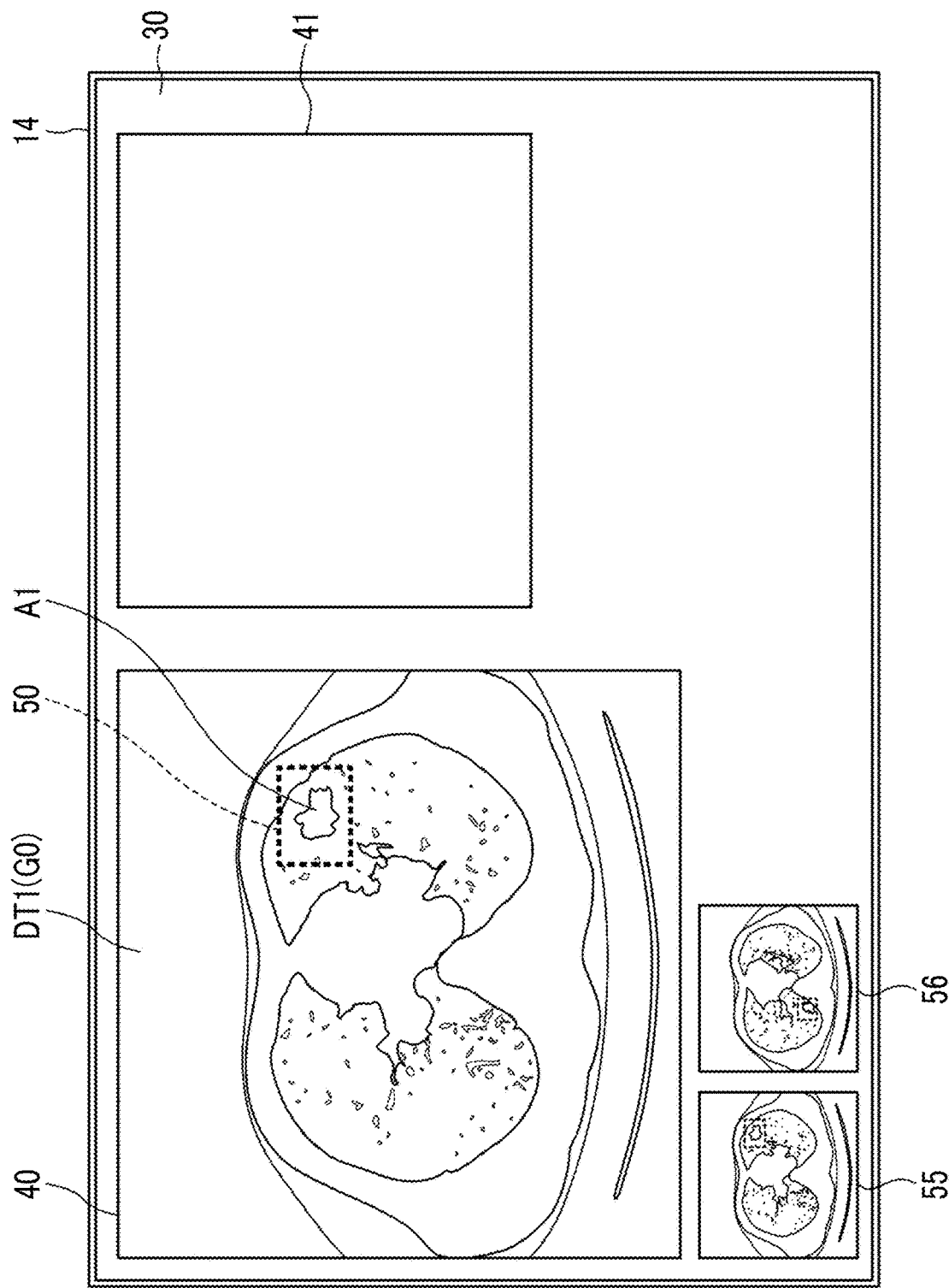
FIG. 5 is a diagram showing a screen for creating an interpretation report according to each exemplary embodiment.

FIG. 5 is a diagram showing an example of the interpretation report creation screen 30 displayed on the display unit 14. As shown in FIG. 5, the creation screen 30 includes an image display region 40 in which the medical image G0 is displayed, and an input region 41 in which the content of comments on findings input by the radiologist via the input unit 15 is displayed. In the example of FIG. 5, the tomographic image DT1 including the feature region including the nodular shadow A1 is displayed in the image display region 40.

In a case where a plurality of feature regions are extracted by the extraction unit 22, a tomographic image including each feature region may be displayed as a thumbnail on the creation screen 30. For example, the creation screen 30 of FIG. 5 includes a thumbnail 55 of the tomographic image DT1 including the feature region including the nodular shadow A1 and a thumbnail 56 of the tomographic image DT2 including the feature region including the infiltration shadow A2. In this case, the radiologist may select a thumbnail of the tomographic image to be displayed in the image display region 40 via the input unit 15, and the display control unit 25 may perform control such that the tomographic image corresponding to the selected thumbnail is displayed in the image display region 40.

Figure 6:
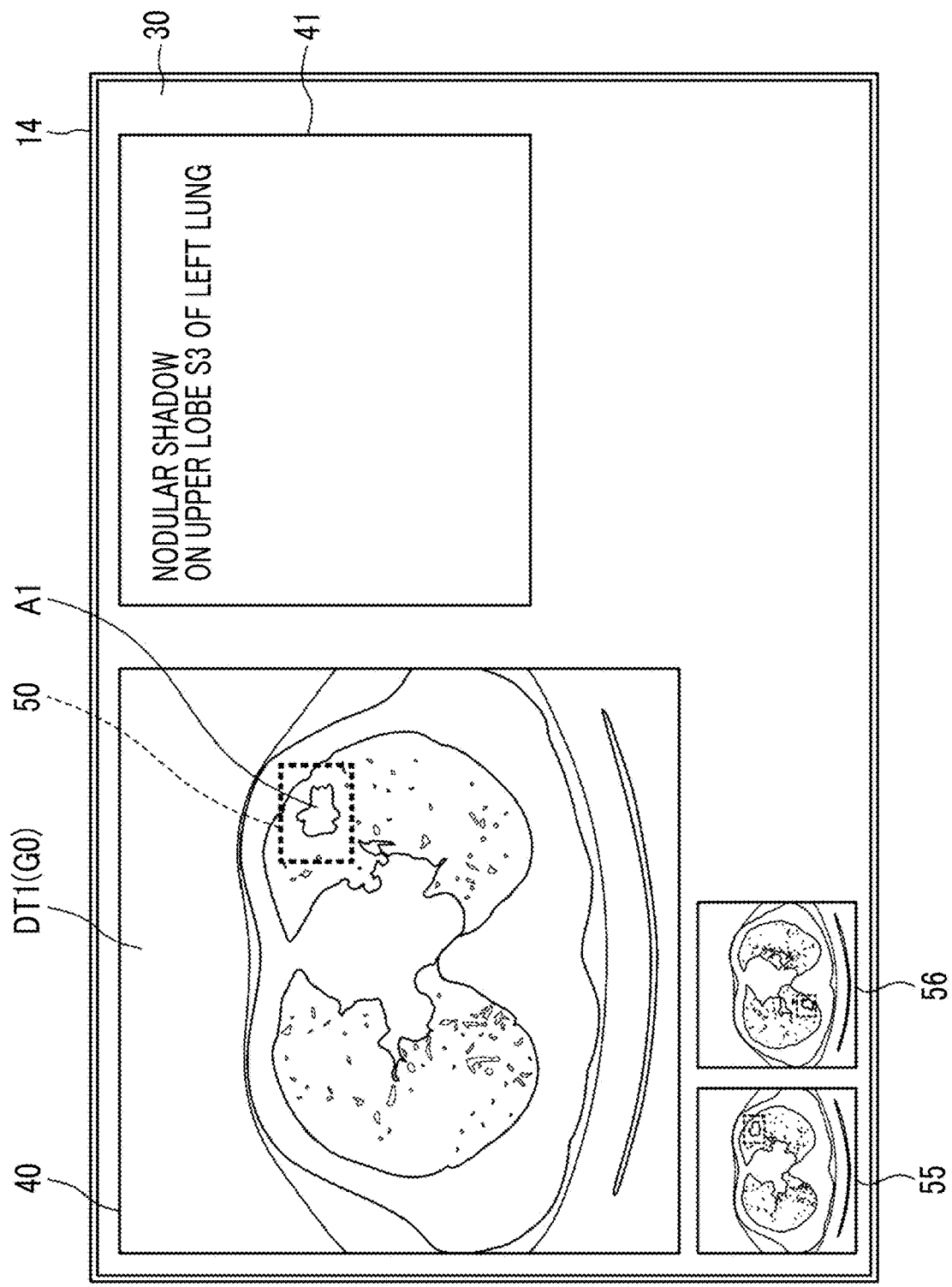
FIG. 6 is a diagram showing a screen for creating an interpretation report according to each exemplary embodiment.

FIG. 6 is a diagram showing the creation screen 30 in a state in which the content of the input comments on findings is displayed. In a case where the radiologist inputs "nodular shadow on the upper lobe S3 of left lung" via the input unit 15, the display control unit 25 performs control such that a character string "nodular shadow on the upper lobe S3 of left lung" is displayed in the input region 41. Further, the specifying unit 23 specifies the feature region including the nodular shadow A1 as a specific region corresponding to the phrase "nodular shadow".

Figure 7:
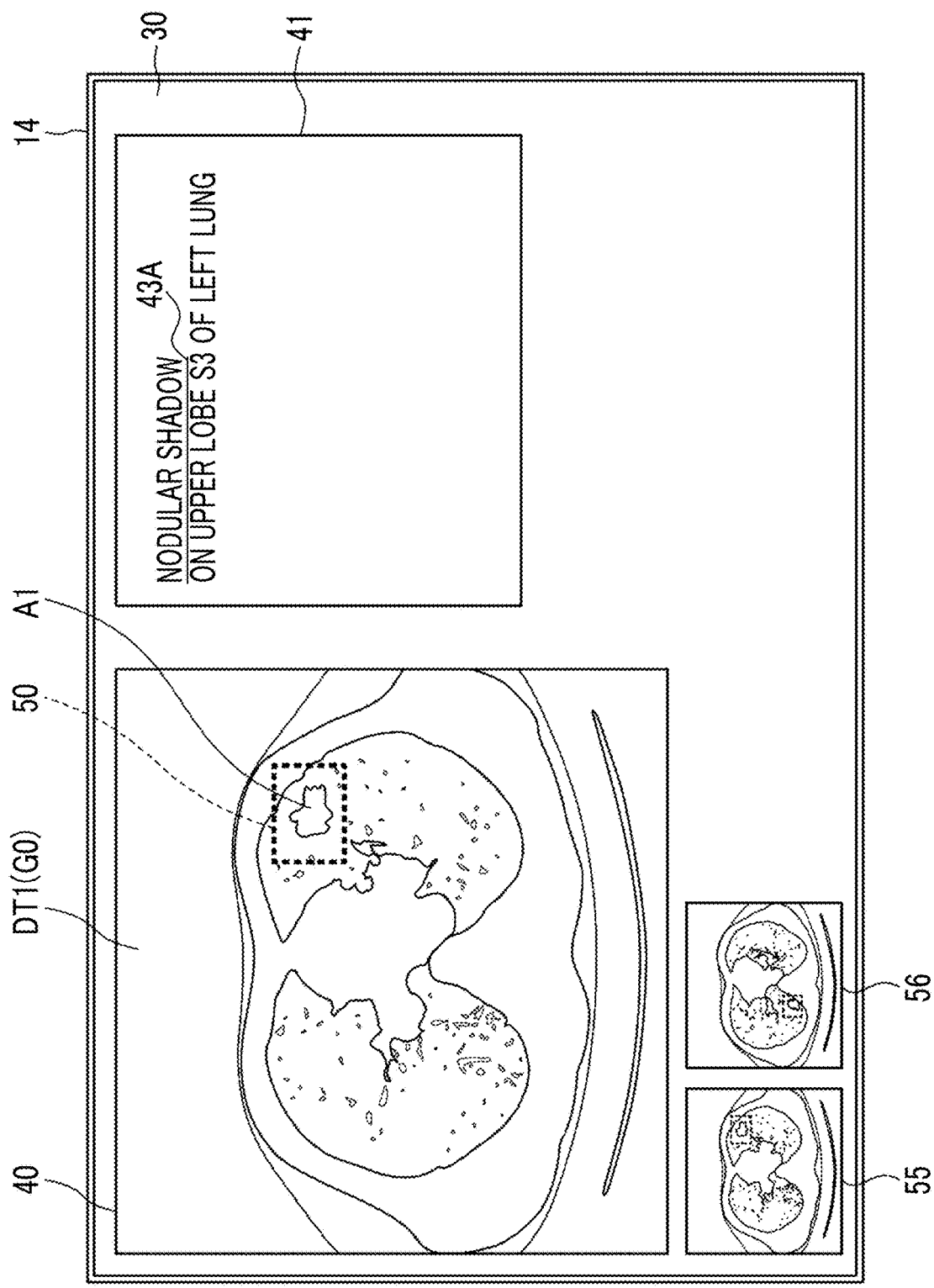
FIG. 7 is a diagram showing an example of support information according to a first exemplary embodiment.

Next, with reference to FIGS. 7 and 8, the support for creating the interpretation report via the document creation support apparatus 20 according to a first exemplary embodiment and the support information will be described in detail. FIG. 7 is a diagram showing the creation screen 30 on which comments on findings to which a hyperlink is added as an example of the support information are displayed.

The generation unit 24 generates a hyperlink 43A for the tomographic image DT1 as an example of information for accessing the tomographic image DT1 including the specific region corresponding to the phrase "nodular shadow". Further, the generation unit 24 embeds the generated hyperlink 43A for the tomographic image DT1 in the phrase "nodular shadow" in the comments on findings. The hyperlink 43A may include a uniform resource locator (URL) indicating a storage location of the tomographic image DT1. The information for accessing the tomographic image DT1 is not limited to the hyperlink, and, for example, the coordinate position of the tomographic image DT1 in the medical image G0 may be used.

The display control unit 25 performs control such that the comments on findings in which the hyperlink 43A for the tomographic image DT1 is embedded in the phrase "nodular shadow" by the generation unit 24 are displayed on the display unit 14. Thereby, in the example of FIG. 7, the tomographic image DT1 can be accessed by selecting the phrase "nodular shadow" in the comments on findings.

Figure 8:
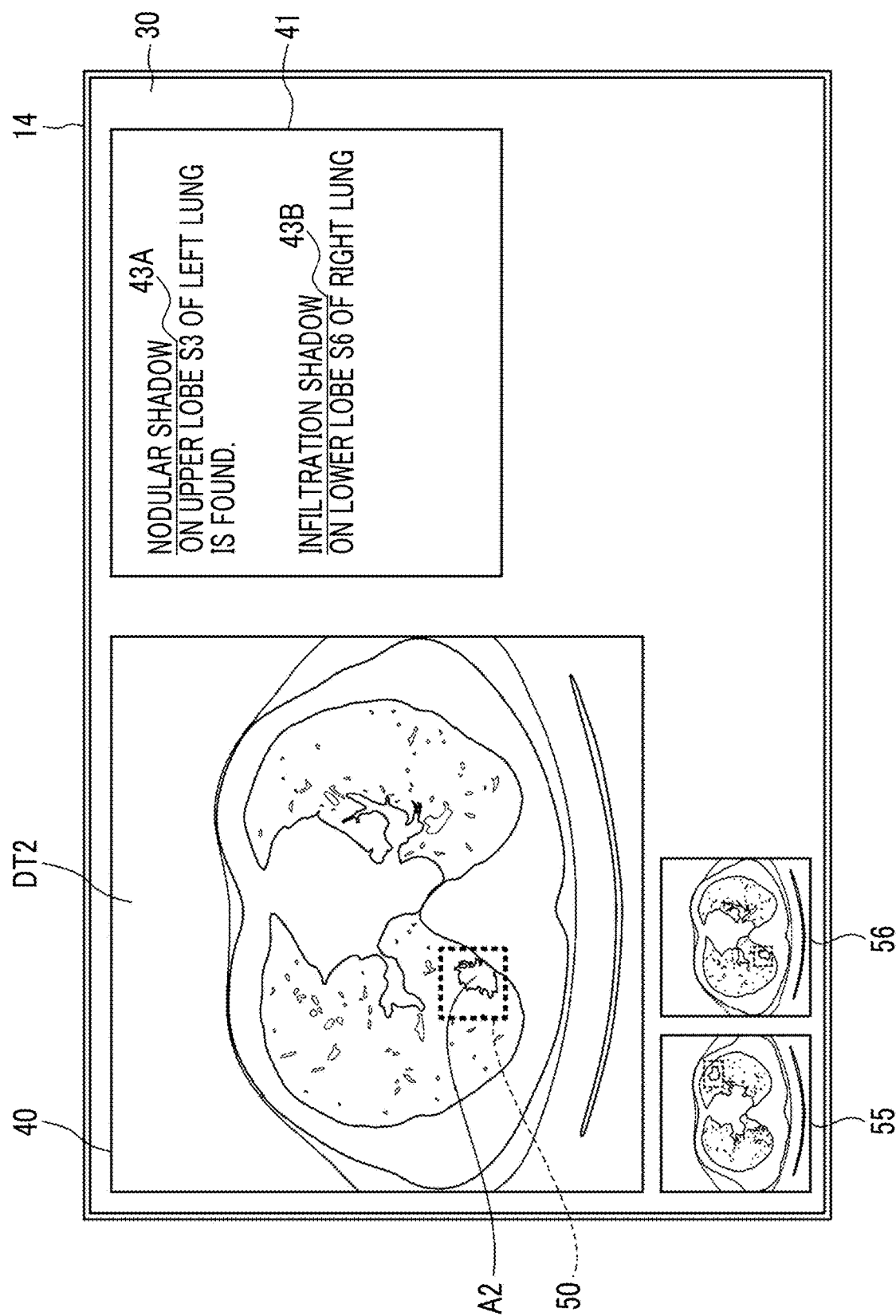
FIG. 8 is a diagram showing an example of support information according to the first exemplary embodiment.

FIG. 8 is a diagram showing the creation screen 30 in a case where the radiologist further adds comments on findings. As shown in FIG. 8, in a case where the radiologist inputs "infiltration shadow on the lower lobe S6 of right lung" via the input unit 15, the specifying unit 23 specifies the feature region including the infiltration shadow A2 as a specific region corresponding to the phrase "infiltration shadow".

The generation unit 24 generates a hyperlink 43B for the tomographic image DT2 including the specific region corresponding to the phrase "infiltration shadow". Further, the generation unit 24 embeds the generated hyperlink 43B for the tomographic image DT2 in the phrase "infiltration shadow" in the comments on findings. The hyperlink 43B may include a URL indicating a storage location of the tomographic image DT2.

The display control unit 25 performs control such that the comments on findings in which the hyperlink 43B for the tomographic image DT2 is embedded in the phrase "infiltration shadow" by the generation unit 24 are displayed on the display unit 14. Thereby, in the example of FIG. 8, the tomographic image DT2 can be accessed by selecting the phrase "infiltration shadow" in the comments on findings. In this case, as shown in FIG. 8, the display control unit 25 performs control such that the tomographic image DT2 is displayed in the image display region 40.

The information for accessing the image including the specific region generated by the generation unit 24 as described above is included in the interpretation report and is registered in the report DB 8. Therefore, even in a case where the interpretation report is viewed from the interpretation WS 3 and the medical care WS 4, it is possible to select the phrase in the comments on findings, thereby accessing the image including the specific region corresponding to the phrase.

Figure 9:
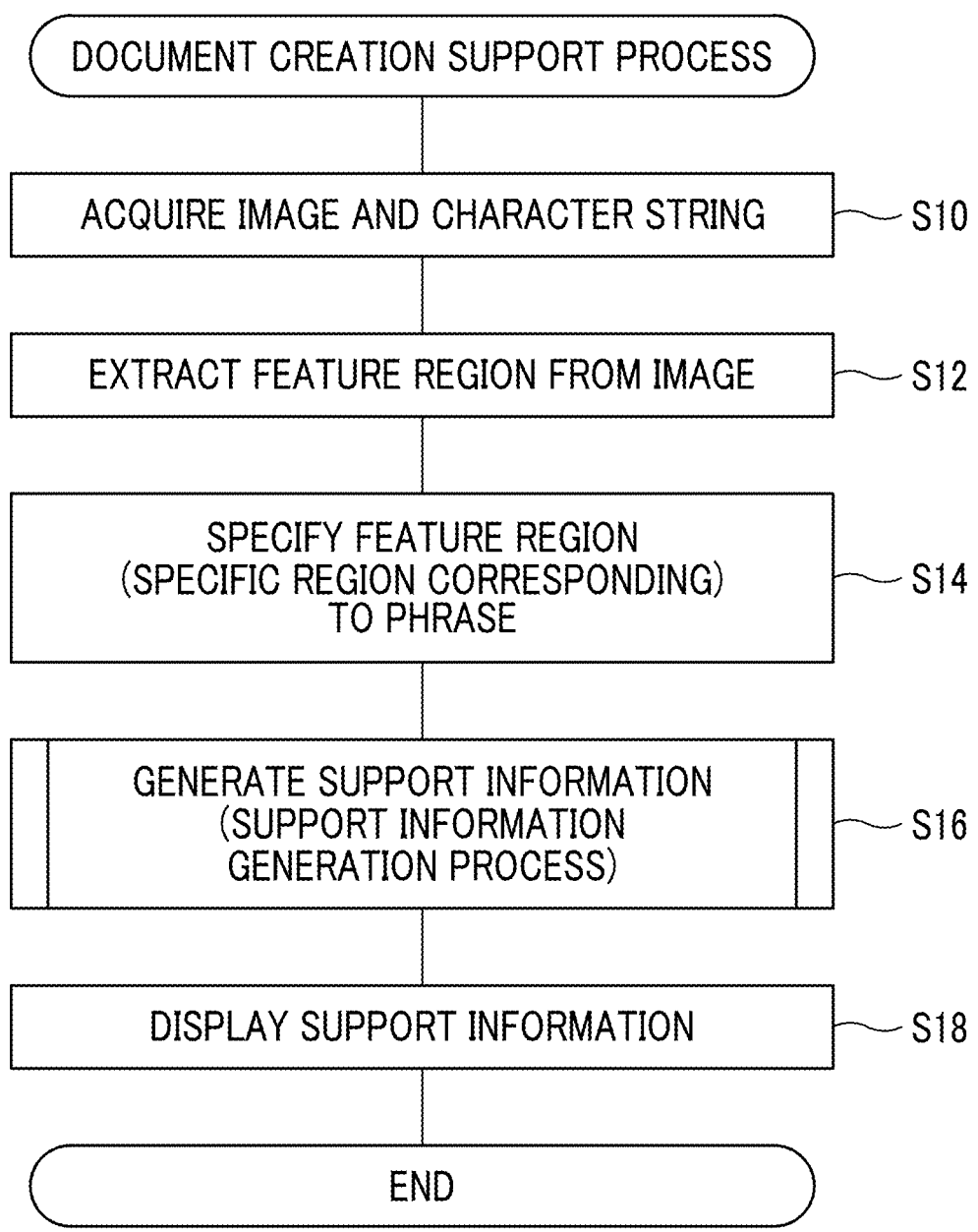
FIG. 9 is a flowchart showing an example of a document creation support process according to each exemplary embodiment.

Next, with reference to FIG. 9, operations of the document creation support apparatus 20 according to the present exemplary embodiment will be described. With CPU 11 executing the document creation support program 12, a document creation support process shown in FIG. 9 is executed. The document creation support process shown in FIG. 9 is executed, for example, in a case where an instruction to start creating an interpretation report for the medical image G0 is input via the input unit 15.

In Step S10 of FIG. 9, the acquisition unit 21 acquires the medical image G0 from the image server 5 and acquires the comments on findings regarding the medical image G0 input via the input unit 15. In Step S12, the extraction unit 22 extracts at least one feature region included in the medical image G0 acquired in Step S10. In Step S14, the specifying unit 23 specifies a specific region, which is a region corresponding to a phrase included in the comments on findings acquired in Step S10, in the feature region extracted in Step S12.

In Step S16, the generation unit 24 generates support information for supporting the creation of the interpretation report based on the result specified in Step S14. In Step S18, the display control unit 25 controls the content to be displayed on the display unit 14 based on the support information generated in Step S16, and ends the process.

Figure 10:
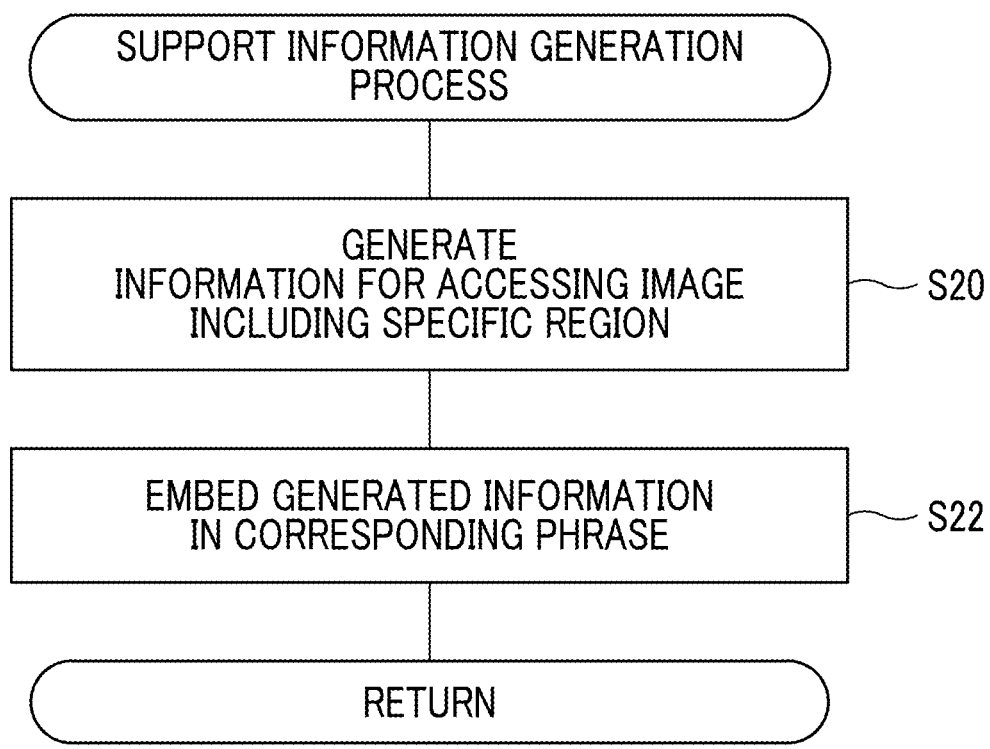
FIG. 10 is a flowchart showing an example of a support information generation process according to the first exemplary embodiment.

FIG. 10 is a flowchart showing details of a support information generation process according to the first exemplary embodiment, which is performed in Step S16 of FIG. 9. In Step S20, the generation unit 24 generates information for accessing the image including the specific region specified in Step S14 as the support information. In Step S22, the generation unit 24 embeds information for accessing the image including the specific region generated in Step S20 in the phrase corresponding to the specific region included in the comments on findings.

As described above, with the document creation support apparatus 20 according to the present exemplary embodiment, the medical image G0 and the comments on findings related to the medical image G0 are acquired, at least one feature region included in the medical image G0 is extracted, a specific region, which is a region corresponding to the phrase included in the comments on findings, is specified in the feature region, information for accessing the medical image G0 including the specific region is embedded in the phrase corresponding to the specific region in the comments on findings, as the information for supporting creation of the document including the comments on findings, based on a result of the specifying, and the embedded information is displayed on the display unit. Therefore, it is possible to create an interpretation report so that it is possible to know which tomographic image in the medical image G0 can be used to recognize the findings described in the interpretation report, regardless of the manual input of the radiologist, and thus it is possible to support creation of documents such as the image interpretation report.

In the present exemplary embodiment, the comments on findings acquired by the acquisition unit 21 are input by the radiologist via the input unit 15, but the present disclosure is not limited thereto. For example, JP2013-39230A discloses a technique for using a discriminator trained to output comments on findings for size and shape of a lesion and presumed disease name, or the like by inputting an analysis result by CAD to generate the comments on findings from an analysis result by CAD. This technique may be applied to the present exemplary embodiment so that the extraction unit 22 extracts a feature region from the medical image G0 acquired by the acquisition unit 21 and generates comments on findings from the extracted feature region. Further, a technique for generating comments on findings based on a fixed form, which is disclosed in JP1995-31591A (JP-H7-31591A), may be applied. With the form in which the comments on findings are automatically generated in this way, it is possible to support the creation of a document such as an interpretation report, and thus it is possible to reduce the burden on the radiologist at the time of creating the interpretation report.

Further, in the present exemplary embodiment, in a case where there is another image corresponding to the medical image G0 including the specific region, information for accessing the other image may be embedded in a phrase corresponding to the specific region in comments on findings and may be displayed on the display unit. For example, in a case where a follow-up observation is performed on the nodular shadow A1, information for accessing a tomographic image captured in the past corresponding to the tomographic image DT1 including the nodular shadow A1 may be embedded in the phrase "nodular shadow" in the comments on findings and may be displayed on the display unit. With such a form, it is possible to support creation of a document such as an interpretation report in a case where the follow-up observation is performed.

Second Exemplary Embodiment

Next, a second exemplary embodiment of the present disclosure will be described. In the present exemplary embodiment, the content of the support information generated by the generation unit 24 and the display content on the creation screen 30 displayed on the display unit 14 by the display control unit 25 based on the support information are different from those of the first exemplary embodiment. The configuration of the medical information system 1 (see FIG. 1), the hardware configuration of the document creation support apparatus 20 (see FIG. 2), and the functional configuration (see FIG. 3) according to the present exemplary embodiment are the same as those in the first exemplary embodiment, and thus the description thereof will be omitted.

Figure 11:
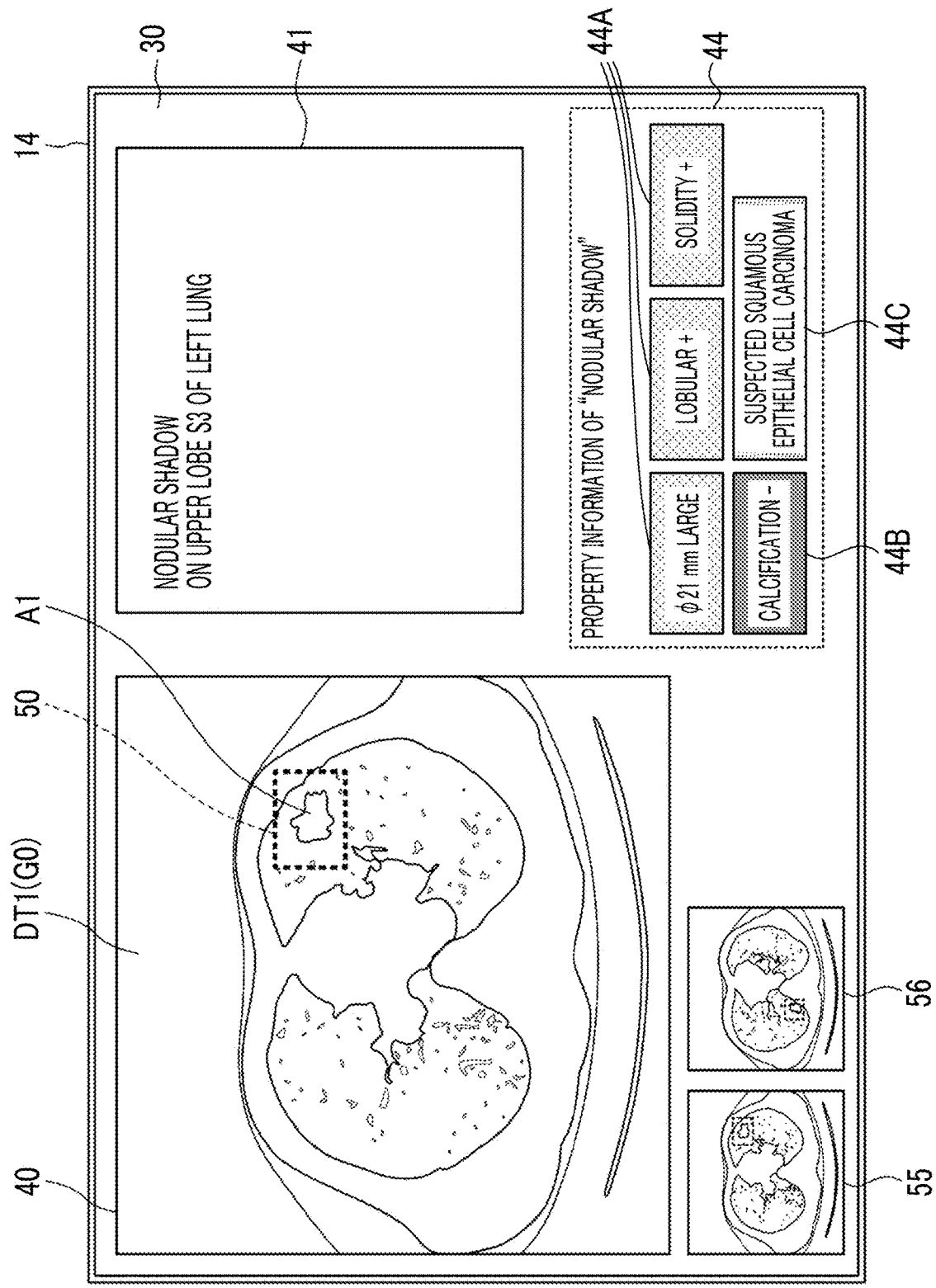
FIG. 11 is a diagram showing an example of support information according to a second exemplary embodiment.

With reference to FIG. 11, the support for creating the interpretation report via the document creation support apparatus 20 according to the second exemplary embodiment and the support information will be described in detail. FIG. 11 is a diagram showing the creation screen 30 on which property information 44 indicating the property of a specific region is displayed as an example of the support information.

The generation unit 24 generates the property information 44 indicating a property of a specific region corresponding to a phrase included in the character string. The display control unit 25 performs control such that the property information 44 generated by the generation unit 24 is displayed on the display unit 14. Here, the property of the specific region indicates, for example, the property such as the position, size, and shape of the structure included in the specific region. In addition, the generation unit 24 may generate property information 44 regarding a presumed disease name suspected in a specific region based on properties such as the position, size, and shape of the structure.

For example, the generation unit 24 analyzes a specific region including the nodular shadow A1 in the tomographic image DT1 via CAD or the like in response to the phrase "nodular shadow", and generates the property information 44 indicating the properties of the nodular shadow A1 included in the specific region. As an example of the property information 44, the generation unit 24 generates positive information 44A for "φ21 mm large", "lobular+", and "solidity+", negative information 44B for "calcification−", and disease name information 44C for "suspected squamous epithelial cell carcinoma". Here, the property information to which "+" is added indicates that the property is positive, and the property information to which "−" is added indicates that the property is negative.

As a method for generating the property information 44 via the generation unit 24, for example, a method described in Literature 1 above can be used, but the method is not limited thereto.

Figure 12:
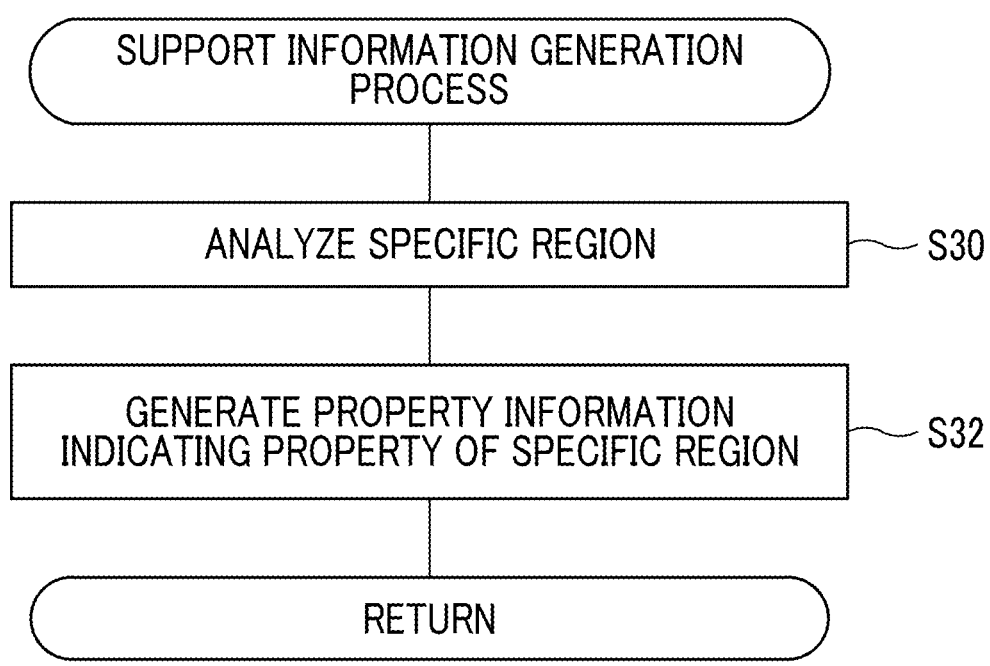
FIG. 12 is a flowchart showing an example of a support information generation process according to the second exemplary embodiment.

FIG. 12 is a flowchart showing details of a support information generation process according to the second exemplary embodiment, which is performed in Step S16 of FIG. 9. In Step S30, the generation unit 24 analyzes the specific region specified in Step S14. In Step S32, the generation unit 24 generates property information indicating the property of the specific region as the support information based on the analysis.

As described above, with the document creation support apparatus 20 according to the present exemplary embodiment, the medical image G0 and the comments on findings related to the medical image G0 are acquired, at least one feature region included in the medical image G0 is extracted, a specific region, which is a region corresponding to the phrase included in the comments on findings, is specified in the feature region, property information indicating the property of the specific region is generated, as the information for supporting creation of the document including the comments on findings, based on a result of the specifying, and the property information is displayed on the display unit. Therefore, the radiologist can check the property of the specific region before creating the comments on findings regarding the property of the specific region, which makes it is possible to suppress the oversight of the finding and to support creation of a document such as the interpretation report.

In the present exemplary embodiment, the display control unit 25 may change each display method so that the property information 44 can be distinguished from between the positive information 44A, the negative information 44B, and the disease name information 44C. For example, as shown in FIG. 11, a background color may be changed for each of the positive information 44A, the negative information 44B, and the disease name information 44C. With such a form, the user can easily know whether the various property information 44 is a positive, a negative, or a presumed disease name.

Further, in the present exemplary embodiment, the form in which the generation unit 24 generates the property information 44 has been described, but the present disclosure is not limited thereto. For example, the extraction unit 22 may extract the feature region from the medical image G0 and generate the property information 44 about the feature region in advance. In this case, after the phrases included in the character string are acquired, the property information 44 can be displayed on the display unit 14 without analyzing the specific region via CAD or the like.

Further, in the present exemplary embodiment, the property information 44 is not limited to the positive information 44A, the negative information 44B, and the disease name information 44C as shown in FIG. 11. For example, JP2013-39230A discloses a technique for using a discriminator trained to output comments on findings for size and shape of a lesion and presumed disease name, or the like by inputting an analysis result by CAD to generate the comments on findings from an analysis result by CAD. The technique may be applied to the present exemplary embodiment to take a form in which comments on findings indicating a property of a specific region are generated as the property information 44. Further, a technique for generating comments on findings based on a fixed form, which is disclosed in JP1995-31591A (JP-H7-31591A), may be applied. With the form in which the comments on findings are automatically generated in this way, it is possible to support the creation of a document such as an interpretation report, and thus it is possible to reduce the burden on the radiologist at the time of creating the interpretation report.

Third Exemplary Embodiment

Next, a third exemplary embodiment of the present disclosure will be described. In the present exemplary embodiment, the content of the support information generated by the generation unit 24 and the display content on the creation screen 30 displayed on the display unit 14 by the display control unit 25 based on the support information are different from those of the first exemplary embodiment. The configuration of the medical information system 1 (see FIG. 1), the hardware configuration of the document creation support apparatus 20 (see FIG. 2), and the functional configuration (see FIG. 3) according to the present exemplary embodiment are the same as those in the first exemplary embodiment, and thus the description thereof will be omitted.

Figure 13:
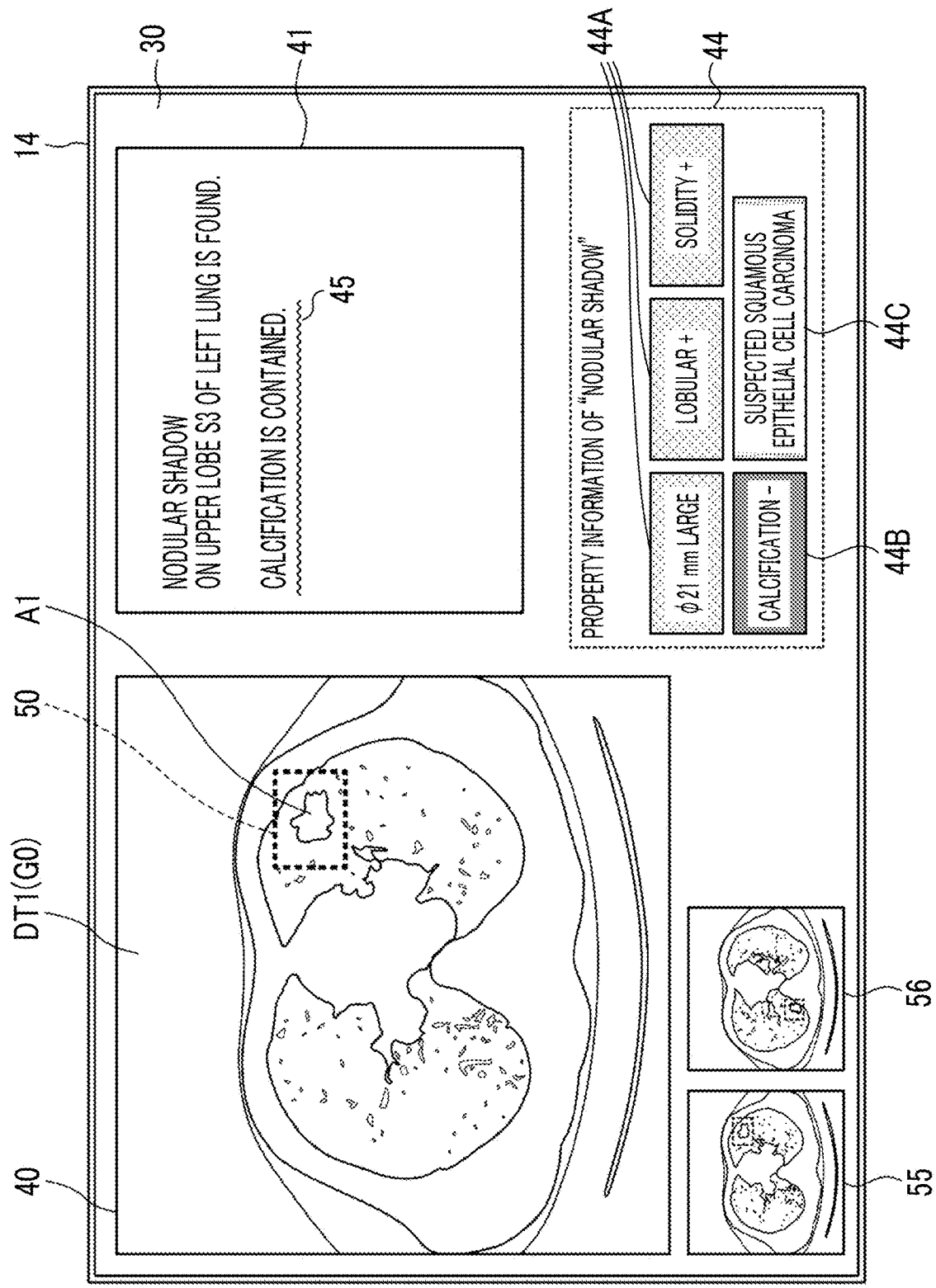
FIG. 13 is a diagram showing an example of support information according to a third exemplary embodiment.

With reference to FIG. 13, the support for creating the interpretation report via the document creation support apparatus 20 according to the third exemplary embodiment and the support information will be described in detail. FIG. 13 is a diagram showing the creation screen 30 on which property information 44 indicating the property of a specific region and a warning 45 based on the property information 44 are displayed as an example of the support information. The property information 44 is the same as that of the second exemplary embodiment, and thus the description thereof will be omitted. The example of FIG. 13 shows a form in which the property information 44 is displayed on the creation screen 30, but the property information 44 may not be displayed on the creation screen 30.

The generation unit 24 generates the property information 44 indicating a property of a specific region corresponding to the phrase included in the character string, and generates warning information for giving the warning 45 in a case where the phrase related to the specific region in the character string does not match the property information 44. The display control unit 25 performs control such that the warning 45 is displayed on the display unit 14 based on the warning information generated by the generation unit 24. Here, the property information 44 is the same as that of the second exemplary embodiment, and thus the description thereof will be omitted.

For example, the generation unit 24 generates negative information 44B for "calcification—" as the property information 44 about a specific region corresponding to the phrase "nodular shadow". Next, the phrase "Calcification is contained." related to the specific region acquired by the acquisition unit 21 is analyzed, and it is determined that the content does not match the negative information 44B of "calcification—". Then, warning information for giving the warning 45 that displays a wavy line under the phrase "Calcification is contained." is generated.

The method for the warning 45 is not limited to displaying a wavy line under a phrase that does not match the property information 44, and, for example, techniques such as changing the color of the phrase, displaying a pop-up screen, sounding an alarm, or the like may be used.

Figure 14:
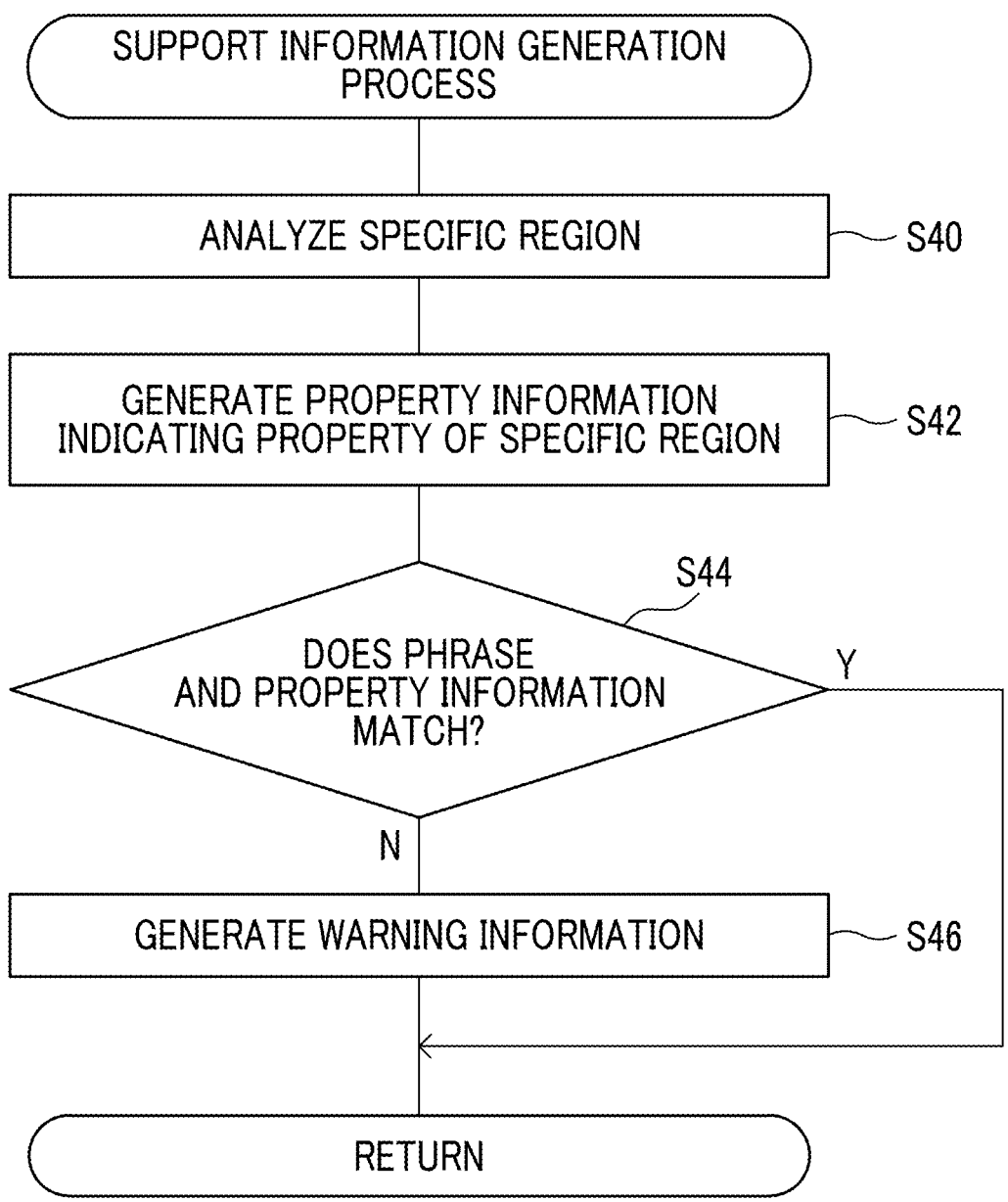
FIG. 14 is a flowchart showing an example of a support information generation process according to the third exemplary embodiment.

FIG. 14 is a flowchart showing details of a support information generation process according to the third exemplary embodiment, which is performed in Step S16 of FIG. 9. In Step S40, the generation unit 24 analyzes the specific region specified in Step S14. In Step S42, the generation unit 24 generates property information indicating the property of the specific region based on the analysis. In Step S44, the generation unit 24 determines whether or not the phrase corresponding to the feature region included in the comments on findings and the property information generated in Step S42 match. In a case where it is determined that the two match, the generation unit 24 terminates the present routine. On the other hand, in a case where it is determined that the two do not match, the generation unit 24 generates warning information for warning that the two do not match in Step S46 as the support information.

As described above, with the document creation support apparatus 20 according to the present exemplary embodiment, the medical image G0 and the comments on findings related to the medical image G0 are acquired, at least one feature region included in the medical image G0 is extracted, a specific region, which is a region corresponding to the phrase included in the comments on findings, is specified in the feature region, property information indicating the property of the specific region is generated, as the information for supporting creation of the document including the comments on findings, based on a result of the specifying, and a warning is given in a case where the phrase related to the specific region in the character string does not match the property information. Therefore, it is possible to suppress misdiagnosis by the radiologist and to support creation of a document such as the interpretation report.

In each of the above exemplary embodiments, the processes of the generation unit 24 and the display control unit 25 described in each of the first exemplary embodiment, the second exemplary embodiment, and the third exemplary embodiment may be performed in an appropriately combined form.

Further, in each of the above exemplary embodiments, the generation unit 24 may generate an image in which a mark indicating the position of the specific region is added to the medical image G0 including the specific region. For example, in the examples of FIGS. 7, 11, and 13, in the tomographic image DT1, the specific region corresponding to the phrase "nodular shadow" specified by the specifying unit 23 is surrounded by a broken-line rectangle 50. Further, for example, in the example of FIG. 8, in the tomographic image DT2, the specific region corresponding to the phrase "infiltration shadow" specified by the specifying unit 23 is surrounded by the broken-line rectangle 50. This makes it easier, for example, for a reader of the interpretation report to see the region in the image that is the basis of the abnormal shadow, without the need for the radiologist to provide comments on findings related to the position of the abnormal shadow. In addition, this makes it easier for the reader of the interpretation report to see which abnormal shadow is the region that is the basis of the comments on findings, even in a case where a plurality of abnormal shadows are found in the same tomographic image. Therefore, it is possible to support creation of a document such as the interpretation report.

Further, in each of the above exemplary embodiments, the generation unit 24 may generate an image in which a mark indicating the position of the feature region is added to the medical image G0 including the feature region. For example, in the examples of FIGS. 5 and 6, in the tomographic image DT1, the feature region including the nodular shadow A1 extracted by the extraction unit 22 is surrounded by the broken-line rectangle 50. In a case where a plurality of feature regions are included in the same tomographic image, each image with a mark indicating the position of each feature region may be generated, or one image with marks indicating the positions of respective feature regions may be generated. This makes it possible, for example, for the position of the feature region to be easily displayed on the display unit 14 before the comments on findings are input by the radiologist, and thus, it is possible to suppress oversight of an abnormal shadow by the radiologist, and it is possible to support creation of a document such as the interpretation report.

The mark indicating the positions of the specific region and the feature region is not limited to the broken-line rectangle 50, but may be various marks such as, for example, a polygon, a circle, an arrow, or the like, and the line type of the mark (for example, a solid line, a broken line, and a dotted line), line color, line thickness, or the like may be changed as appropriate.

Further, in each of the above exemplary embodiments, each process of the extraction unit 22, the specifying unit 23, and the generation unit 24 in the document creation support apparatus 20 encompassed in the interpretation WS 3 may be performed by an external apparatus, for example, another analysis server connected to the network 10. In this case, the external apparatus receives the character string from the document creation support apparatus 20, acquires the medical image G0 corresponding to the character string from the image server 5, extracts the feature region from the medical image G0, specifies the specific region from the character string and the feature region, and generates the support information based on a result of the specifying. The document creation support apparatus 20 transmits the character string acquired by the acquisition unit 21 to the external apparatus, and controls the display content to be displayed on the display unit 14 by the display control unit 25 based on the support information generated by the external apparatus.

Further, in each of the above exemplary embodiments, a known voice input system may be applied to the document creation support apparatus 20 to input the character string related to the medical image G0 by voice.

Further, in each of the above exemplary embodiments, the present disclosure is applied at the time of creating an interpretation report as a document, but the present disclosure may be applied at the time of creating medical documents other than the interpretation report, such as an electronic medical record and a diagnostic report, and documents containing character string related to other images.

Further, in each of the above exemplary embodiments, although the interpretation report creation support process is performed using a medical image G0 with the lung as the diagnosis target, the diagnosis target is not limited to the lung. In addition to the lung, any part of a human body such as a heart, liver, brain, and limbs can be diagnosed.

In each of the above exemplary embodiments, for example, as hardware structures of processing units that execute various kinds of processing, such as the acquisition unit 21, the extraction unit 22, the specifying unit 23, the generation unit 24, and the display control unit 25, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor. As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

The disclosure of Japanese Patent Application No. 2019-217419 filed on Nov. 29, 2019 is incorporated herein by reference in its entirety. Further, all literatures, patent applications, and technical standards described herein are incorporated by reference to the same extent as if the individual literatures, patent applications, and technical standards were specifically and individually stated to be incorporated by reference.

What is claimed is:

1. A document creation support apparatus comprising at least one processor, wherein the processor is configured to:
   acquire an image and a character string related to the image;
   extract at least one feature region included in the image;
   specify a specific region that is a region corresponding to a phrase included in the character string, in the feature region;
   generate support information by analyzing the specific region to specify each properties of the specific region to generate property information comprising a specified result for each of the properties of the specific region for supporting creation of a document, wherein the document is an interpretation report including the character string;
   display a creation screen on a display unit and control display content of the creation screen to display the property information as the support information for supporting creation of the document.

2. The document creation support apparatus according to claim 1, wherein the processor is configured to:
   embed information for accessing the image including the specific region in a phrase corresponding to the specific region in the character string; and
   display the information on the display unit.

3. The document creation support apparatus according to claim 1, wherein the processor is configured to:
   give a warning in a case where a phrase related to the specific region in the character string does not match the property information.

4. The document creation support apparatus according to claim 1, wherein the processor is configured to generate the image in which a mark indicating a position of the specific region is added to the image including the specific region.

5. The document creation support apparatus according to claim 1, wherein the processor is configured to extract the feature region based on at least one of a position, type, or size of a structure included in the image.

6. A document creation support method comprising:
   acquiring an image and a character string related to the image;
   extracting at least one feature region included in the image;
   specifying a specific region that is a region corresponding to a phrase included in the character string, in the feature region;
   generating support information by analyzing the specific region to specify each properties of the specific region to generate property information comprising a specified result for each of the properties of the specific region for supporting creation of a document, wherein the document is an interpretation report including the character string;
   displaying a creation screen on a display unit and controlling display content of the creation screen to display the property information as the support information for supporting creation of the document.

7. A non-transitory computer-readable storage medium storing a document creation support program for causing a computer to execute a process comprising:
   acquiring an image and a character string related to the image;
   extracting at least one feature region included in the image;
   specifying a specific region that is a region corresponding to a phrase included in the character string, in the feature region;
   generating support information by analyzing the specific region to specify each properties of the specific region to generate property information comprising a specified result for each of the properties of the specific region for supporting creation of a document, wherein the document is an interpretation report including the character string;
   displaying a creation screen on a display unit and controlling display content of the creation screen to display the property information as the support information for supporting creation of the document.

8. A document creation support apparatus of claim 1, wherein the processor is further configured to control the display unit to display each properties of the property information comprising a first property having a plus sign indicating a presence of the first property and a second property having a minus sign indicating an absence of the second property.

9. A document creation support apparatus of claim 1, wherein the processor is further configured to generate a warning message in response to a property generated as a part of the property information not matching any word of the character string of the image.

* * * * *